United States Patent [19]

Plessers

[11] Patent Number: 5,518,931
[45] Date of Patent: May 21, 1996

[54] PROCESS FOR DETERMINING THE CONCENTRATION OF A GAS IN A MOLTEN METAL

[75] Inventor: Jaques J. Plessers, Houthalen, Belgium

[73] Assignee: Heraeus Electro-Nite International N.V, Houthalen, Belgium

[21] Appl. No.: 272,436

[22] Filed: Jul. 8, 1994

Related U.S. Application Data

[63] Continuation of Ser. No. 42,034, Apr. 2, 1993, abandoned.

[30] Foreign Application Priority Data

Apr. 3, 1992 [DE] Germany ............ 42 11 041.6

[51] Int. Cl.$^6$ ............ G01N 35/08; G01N 33/20
[52] U.S. Cl. ............ 436/52; 73/19.01; 73/19.07; 436/75; 436/106; 436/144
[58] Field of Search ............ 436/52–53, 50, 436/55, 106, 144, 83, 75; 73/19.01, 19.05, 19.07, 19.12, 19.1, 61.41, 61.43, 64.56; 422/67

[56] References Cited

U.S. PATENT DOCUMENTS

| | | | |
|---|---|---|---|
| 3,859,209 | 1/1975 | Jahnsen et al. | 210/25 |
| 4,731,732 | 3/1988 | Warchol et al. | 73/19.07 |
| 4,757,707 | 7/1988 | Harvey et al. | 73/19.07 |
| 4,907,440 | 3/1990 | Martin et al. | 73/19.07 |
| 5,031,444 | 7/1991 | Doutre et al. | 73/19.07 |

FOREIGN PATENT DOCUMENTS

| | | |
|---|---|---|
| 0238054 | 12/1990 | European Pat. Off. . |
| 1939403 | 2/1970 | Germany . |
| 4012454 | 8/1991 | Germany . |
| WO8807197 | 9/1988 | WIPO . |

*Primary Examiner*—Jill Warden
*Assistant Examiner*—Jan M. Ludlow
*Attorney, Agent, or Firm*—Panitch Schwarze Jacobs & Nadel

[57] ABSTRACT

A process is provided for determining the concentration of a gas in a molten metal by a carrier gas, which can be pumped to at least one analyzer, either in direct route for calibration, or for measuring through a measuring circuit with a measuring probe immersed in the molten metal, wherein the carrier gas effects a gas exchange with the molten metal, and this gas mixture is pumped to the analyzer for measurement. In order to obtain an accurate and quick reading of the concentration of a gas in a molten metal, the carrier gas is pumped for one segment of a measuring cycle directly to the analyzer for calibration, as well as to the measuring circuit for purging and for uptake of the gas to be measured, so that the gas to be measured is ready for the analyzer. Hence, the carrier gas is pumped through the measuring circuit to at least one analyzer, and a partial pressure is calculated after the gas exchange in the molten metal, as a first approximate value for the partial pressure of the gas to be measured from the molten metal.

13 Claims, 2 Drawing Sheets

PROCESS FOR DETERMINING THE CONCENTRATION OF A GAS IN A MOLTEN METAL

This application is a continuation of application Ser. No. 08/042,034, filed Apr. 2, 1993, now abandoned.

FIELD OF THE INVENTION

The invention concerns a process for determining the concentration of a gas in a molten metal by means of a carrier gas, which can be pumped to at least one analyzer, either in direct route for calibration, or for measuring through a measuring circuit with a measuring probe immersed in the molten metal, whereby for measurement the carrier gas effects a gas exchange with the molten metal, and this gas mixture is pumped to the analyzer.

Background of the Invention

Such a process is known from EP 0 238 054. In this publication the measuring of hydrogen, nitrogen and oxygen concentration in molten metal is described. Here, from a gas source, which holds the carrier gas, such as helium or a mixture of helium and the gas to be measured, the carrier gas in its first phase is pumped by way of a multipath valve through an analyzer, whereby the analyzer is purged and calibrated. Then, the carrier gas is led from the gas source through a probe located in the molten metal in which it enters into a gas exchange with the gas to be measured which diffuses from the molten metal into the probe. This gas mixture is then pumped to the analyzer through the multipath valve.

The measuring process described here has the disadvantage, that a gas exchange with the molten metal takes place only after the calibration of the analyzer. Hence, the gas mixture to be measured is not immediately available after calibration, since the path of the gas through the measuring probe's measuring circuit takes a few seconds, whereby the first gas volume which flows through the measuring circuit is not suitable for measuring, since the gas exchange in the measuring circuit also takes a long time, so that the initial gas volume flowing through the analyzer does not represent the concentration of the gas to be measured. With this measuring process the measuring probe must remain a relatively long time in the molten metal. In order to not fail prematurely, the probe must be made especially resistant to the molten metal, that is, as a rule either very expensive materials or cheaper materials with greater thickness must be used. The greater mass of the measuring probe created influences the temperature of the molten metal to a greater degree, so that the equilibrium relationships change, and the measurement can become inaccurate.

It is therefore an object of the present invention to provide a process with which it is possible to determine the concentration of a gas in a molten metal with high speed and great accuracy.

SUMMARY OF THE INVENTION

This object is solved in that for a measuring cycle in one measuring segment the carrier gas can be pumped directly to the analyzer for calibration, as well as to the measuring circuit for purging and for uptake of the gas to be measured, whereby the gas to be measured stands ready at the analyzer. The carrier gas is pumped at least partially through the measuring circuit and partially to the analyzer, and a partial pressure is calculated as the first approximate value for the partial pressure of the gas to be measured in the molten metal. By such a process the analyzer is calibrated, while simultaneously the measuring circuits are purged, and the gas to be measured from the molten metal is taken up, so that immediately after the termination of the calibration, and without unnecessary time delay, the gas to be measured is measured in the analyzer. It is also possible to use various analyzers, e.g., one for the gas pumped directly to the analyzer, and a second one for the gas mixture, which consists of the gas to be measured and the gas running through the measuring circuit. The results of both analyzers are then compared.

A measuring cycle can thereby have one or more measuring segments, whereby the accuracy of the measurement increases with the increasing number of completed measuring segments. Therefore, advantageously in a second measuring segment of the measuring circuit, the calculated value is taken as the ideal value for a partial pressure to be set for the gas mixture, consisting of the carrier gas and a gas to be mixed with the carrier gas, which gas is the same as the gas to be measured. The gas mixture is accordingly set to the ideal value and the actual value of the partial pressure of this gas mixture is measured in the analyzer, while simultaneously this gas mixture is pumped to the measuring circuit for purging and for uptake of the gas to be measured. Then, the partial pressure of the gas mixture is measured after a gas exchange with the molten metal, and thereafter a new approximate value is calculated. By means of this measuring segment, the accuracy of the measurement is increased. Since the gas, which is the same as the gas to be measured, is mixed with the carrier gas, the carrier gas already has a concentration of the gas to be measured, which is close to the equilibrium concentration, which is approached during the gas exchange by the gas in the molten metal.

The accuracy of the process can be further increased if the second measuring segment is followed by additional measuring segments, wherein at any given time at least the new approximate value is used as the ideal value for the partial pressure to be set for the gas mixture, consisting of the carrier gas and the gas to be mixed with the carrier gas, the mixed gas being the same as the gas to be measured. This gas mixture is set according to the ideal value, and then in the analyzer the actual value of the partial pressure of the gas mixture is measured after the gas exchange with the molten metal. Thereafter, a further new approximate value is calculated.

For the measurement of nitrogen in the molten metal, using a sequential measuring cycle, an ideal value for the partial pressure in the first measuring segment is calculated, wherein a constant (B) is derived from a preceding measuring segment which results from the equation:

$$R_1 - S_1 = \frac{(X - S_1)}{B} \qquad (1)$$

wherein:

$R_1$ = partial pressure of the gas to be measured, after the gas exchange in the molten metal in the first measuring segment;

$S_1$ = actual value of the partial pressure measured in the first segment for the gas mixed with the carrier gas which is pumped directly to the analyzer, the mixed gas being the same as the gas to be measured;

X = the measured value of the partial pressure of the gas to be measured in the molten metal.

The setting of the ideal value ($M_2$) of the gas mixture to be set for the second measuring segment results from the equation:

$$S_1 + B(R_1 - S_1) = M_2$$

For further increasing the accuracy of this measuring segment, an ideal value ($M_{j+1}$) for the partial pressure in the (j+1)th measuring segment results from the equation:

$$M_{j+1} = \frac{S_j(R_j - S_j) - S_i(R_j - S_j)}{R_1 - S_i - R_j + S_j} + S_j, \quad (3)$$

wherein i and j represent measurement numbers for the measuring segments, such that the (j)th measuring segment corresponds to the (i+n)th measuring segment, wherein i, j and n are whole numbers greater than zero. This means that for the calculation of $M_{j+1}$, the values $S_j$ and $R_j$ from the immediately preceding (j)th measuring segment are referred to, while the values of $S_i$ and $R_i$ can be used from any preceding measuring segment.

In the case of measuring nitrogen in the molten metal, it can be advantageous that from the constant (B) calculated from a measuring segment in the sequential measuring cycle, the sulfur content of the molten metal is derived using a respective sequential measuring cycle, whereby simultaneously a statement of additional components contained in the molten metal is obtained.

For the measurement of hydrogen in the molten metal using a sequential measuring cycle, an ideal value for the partial pressure in the first measuring segment is calculated, wherein the constant (B') is derived from the preceding measuring cycle, which results from the equation:

$$R_1 - S_1 = \frac{\sqrt{X} - \sqrt{S_1}}{B'} \quad (4)$$

wherein:

$R_1$=partial pressure of the gas to be measured, after the gas exchange in the molten metal in the first measuring segment;

$S_1$=actual value of the partial pressure measured in the first segment for the gas mixed with the carrier gas which is pumped directly to the analyzer, the mixed gas being the same as the gas to be measured;

X=the measured value of the partial pressure of the gas to be measured in the molten metal.

The setting of the ideal value ($M_2$) of the gas mixture to be set for the second measuring segment results from the equation:

$$[\sqrt{S_1} + B'(R_1 - S_1)]^2 = M_2. \quad (5)$$

For further increasing the accuracy of the measurement of hydrogen in the molten metal, it is useful that an ideal value ($M_{j+1}$) for the partial pressure in the (j+1)th measuring segment be derived from the equation:

$$M_{j+1} = \frac{\sqrt{S_i}(R_i - S_i) - \sqrt{S_j}(R_i - S_i)}{R_j - S_j - R_i + S_i} + \sqrt{S_i} \quad (6)$$

wherein i and j represent measurement numbers for the measuring segments, such that the (j)th measuring segment corresponds to the (i+n)th measuring segment wherein i, j and n are whole numbers greater than 0. Here, similar to the measurement of nitrogen, by means of carrying out a series of measuring segments within one measuring cycle, the accuracy can be increased as desired.

It is advantageous that, on the basis of the difference between the actual value of the partial pressure of the gas pumped directly to the analyzer and the ideal value set for the gas mixture, a calibration of the mixing chamber is obtained for adding the mixing gas, which is the same as the gas to be measured, for the next measuring segment. Thereby, the number of necessary measuring segments, which are needed for a high degree of measuring accuracy, is reduced.

In the case that the concentration of the gas to be measured is very low, it is sufficient to mix the carrier gas with a very small amount of the gas which is the same as the gas to be measured. To achieve a better dosability, it is useful that the gas mixed with the carrier gas be a gas mixture of a gas the same as the carrier gas and a gas, the same as the gas to be measured.

For improvement of the calibration of the analyzer it is advantageous that the carrier gas and/or the mixture consisting of the carrier gas and the mixing gas, prior to the direct pumping into the analyzer, be cleaned of foreign substances, such as water, by a filter.

For faster removal of residual gases it is useful that the carrier gas or the gas mixture of the carrier gas and mixing gas prior to the pumping into the analyzer and/or the measuring circuit be pulsatingly surged to thereby remove the residual gases from the preceding measuring cycles or measuring segments quickly and completely.

BRIEF DESCRIPTION OF THE DRAWINGS

The foregoing summary of the invention, as well as the following detailed description of preferred embodiments, will be better understood when read in conjunction with the appended drawings. For the purpose of illustrating the invention, there are shown in the drawings embodiments which are presently preferred, it being understood, however, that the invention is not limited to the specific arrangements and instrumentalities disclosed.

DETAILED DESCRIPTION OF PREFERRED EMBODIMENT

The present invention may be embodied in other specific forms without departing from the spirit or essential attributes thereof and, accordingly, reference should be made to the appended claims, rather than to the foregoing specification as indicating the scope of the invention.

Figure 1:
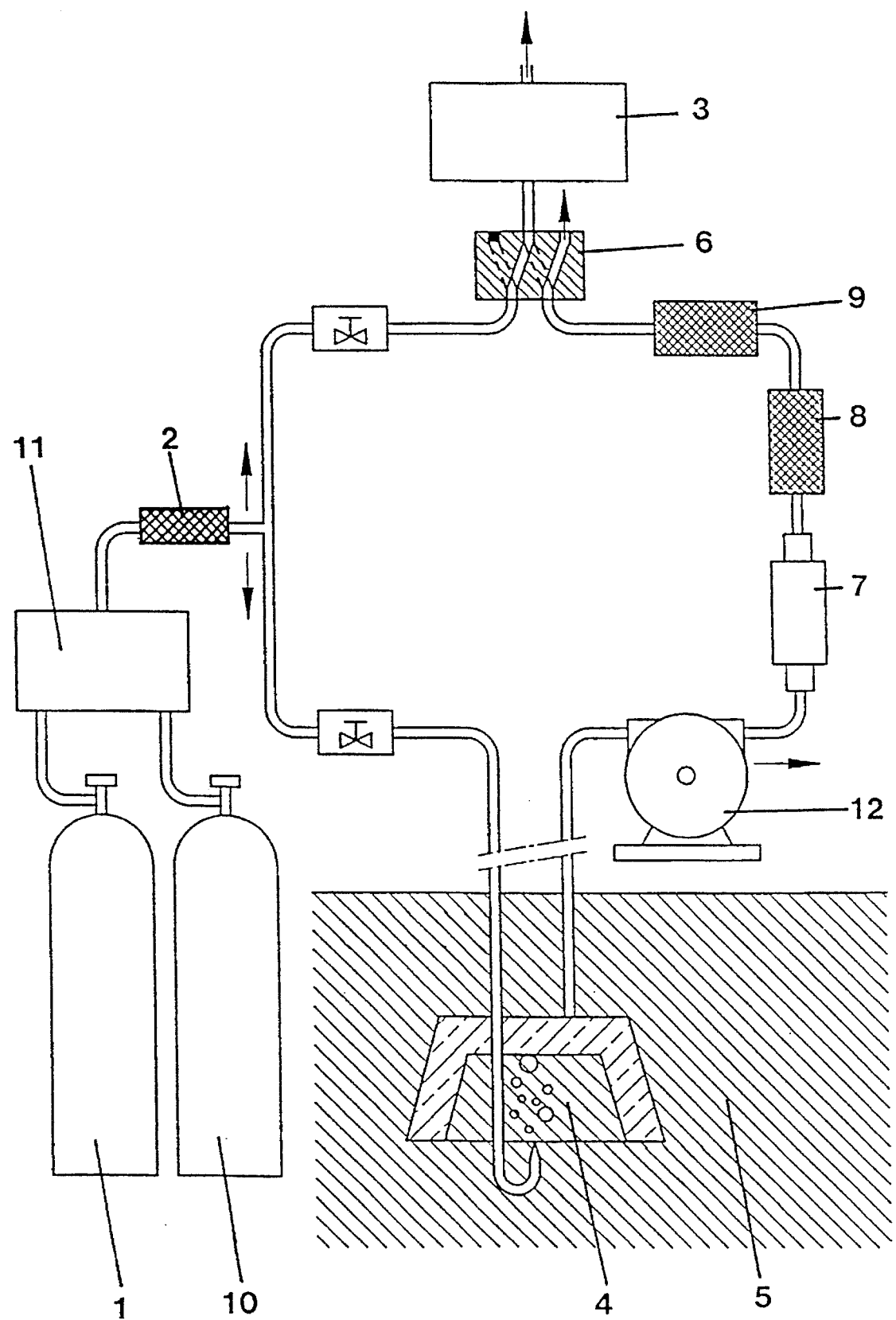
FIG. 1 is a schematic representation of the gas flow path.

The schematically displayed gas flowpath in FIG. 1 reflects the essential measuring construction, as it is used for the measurement of nitrogen in a molten metal, e.g., in a steel melt. Herefore, helium as a carrier gas is pumped from a carrier gas source 1 through a filter 2, in which, if necessary, water or other foreign substances are filtered out, in direct route into the analyzer 3 for calibration, and at the same time into the measuring circuit with the measuring probe 4. Thereby, the measuring circuit is purged at the same time as the calibration of the analyzer 3, and the gas to be measured from the molten metal is taken up into the measuring probe 4 and pumped to a multipath valve 6 switched before the analyzer 3.

During calibration of the analyzer 3, the valve 6 connects the carrier gas source 1 directly with the analyzer 3, while the gas running through the measuring circuit is pumped away through the multipath valve 6. The multipath valve 6 switches after calibration of the analyzer 3, so that the gas mixture, which includes the gas to be measured, flowing through the measuring circuit is pumped to the analyzer 3 for evaluation. A catharometer is used as an analyzer 3. Usually, only a part of the gas mixture which runs through the measuring circuit is pumped to the catharometer.

Since the nitrogen from the molten metal 5 also carries along hydrogen and carbon monoxide, after the gas exchange in the molten metal 5 the gas mixture is pumped through an oxidation tube 7, in which hydrogen is oxidized to water and carbon monoxide to carbon dioxide. The water and carbon dioxide are filtered out through filters 8 and 9, so that only the nitrogen from the molten metal remains in the gas flowing through the measuring circuit, and this gas mixture is pumped into the analyzer 3.

The contact time of the gas, which is pumped through the measuring circuit, and the melt is very short, just as the contact area between the gas bubbles and the melt is small, so that only a limited amount of gas can be exchanged between the gas pumped to the measuring circuit and the melt. Hence, only a first approximate value for the partial pressure of the gas to be measured can be determined in the above described measuring segment.

This first approximate value is an approximate value for the partial pressure of the gas to be measured, as it would be measured after reaching equilibrium in the molten metal 5. This value results from the equation (1), wherein X represents the approximate value, $R_1$ reflects the real measured partial pressure of the gas to be measured after the exchange in the molten metal 5 in the first measuring segment, $S_1$ is the actual value of the partial pressure of the gas mixture pumped directly to the analyzer 3 in the first measuring segment. Theoretically $S_1$ is equal to 0, since in the first measuring segment, the pure carrier gas is pumped directly to the analyzer 3. The constant B is of a size which can be set arbitrarily, whereby according to the degree of deviation of the arbitrarily set constant B from the real circumstances in the molten metal 5, the number needed for an exact measurement can increase in the measuring segments that follow, as described in the following. The constant B can also be determined from the preceding measuring cycle, if the conditions in the molten metal 5 of the preceding measuring cycle and the conditions in the current molten metal 5 to be measured do not differ significantly from each other.

Since the first approximate value, as described, is usually not sufficient for an exact measurement, in the second measuring segment a gas from another gas source 10, which is the same as the gas to be measured, namely, nitrogen or a mixture consisting of helium and nitrogen, is mixed in a gas mixer 11 with the carrier gas (helium). The first measuring segment is repeated with this gas mixture. Hence, this gas mixture is pumped first directly to the analyzer and simultaneously to the measuring circuit, and after calibration of the analyzer 3 the multipath valve 6 is switched, so that the gas mixture is pumped to the analyzer 3 after uptake of the gas to be measured from the molten metal. A pump 12 is used for assisting the gas flow through the measuring circuit. The filter 2 can be placed either immediately after the gas mixer 11 or, for example, between the multipath valve 6 and the analyzer 3. In the latter case, the filter 9 for the filtering out water in the measuring circuit can be omitted.

The proportion of nitrogen to be mixed into the helium from the gas source 10 should be very close to the equilibrium concentration of the nitrogen in the molten metal. This ideal value $M_2$ to be set for the gas mixture can be calculated from equation (2). The ideal value $M_2$ corresponds more exactly to equilibrium conditions in the molten metal, the more constant B has been selected from accurate real conditions. The accuracy of the measured partial pressure of the gas to be measured, after the gas exchange in the molten metal, results from a comparison of this partial pressure with the ideal value. If the needed accuracy lies outside of the predetermined tolerances, then an additional measuring segment is added, in which the ideal value $M_3$ results from the equation (3).

If the difference between the ideal value and the partial pressure of the gas to be measured, after the gas exchange in the molten metal, is within the given tolerances, then this signifies, that an amount of the gas, the same as the gas to be measured (nitrogen), was mixed with the carrier gas (helium) in the gas mixer 11, such that the nitrogen partial pressure of this gas mixture corresponds to the nitrogen partial pressure in the molten metal. Therefore, there is no gas exchange in the molten metal with the gas mixture pumped to the molten metal. Hence, this process is an approximation (trial and error) process, where it is attempted to present a gas mixture, whose nitrogen content corresponds to the nitrogen content in the molten metal, so that a lengthy gas exchange for reaching the equilibrium condition is superfluous and is only required if a gas exchange actually occurs.

Figure 2:
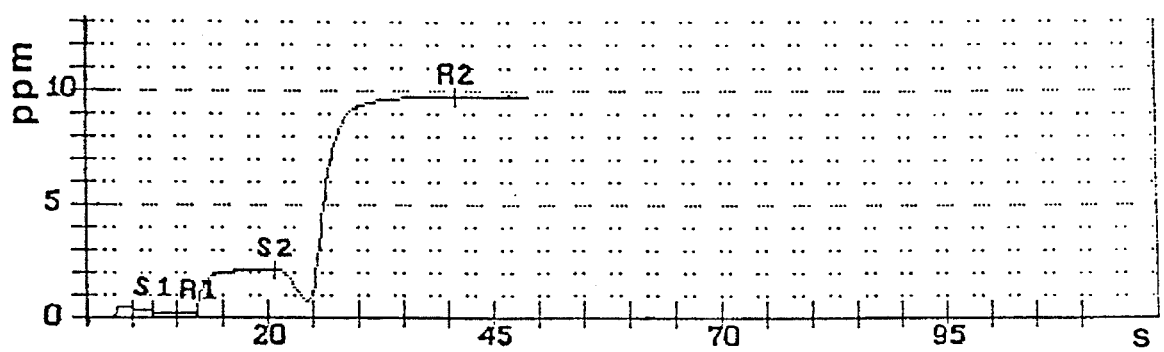
FIG. 2 is a measuring curve produced by the analyzer.

A measurement curve is displayed in FIG. 2, as it was produced according to the above described process. In the first measuring segment no nitrogen is mixed with the helium. Nevertheless, $S_1$ differs slightly from 0, since usually residual gases are in the gas pipes. The residual gases are removed very quickly through pulsating purging of the gas pipes. Starting at the point $R_1$ the measurement of the partial pressure $R_1$ of the gas to be measured after the gas exchange in the molten metal is very small, since the gas exchange is over very quickly and on the basis of the lack of nitrogen in the carrier gas, the equilibrium concentration is definitely not met.

Accordingly, for the calculated ideal value $M_2$ an additional measuring segment is started at point $S_2$, where a nitrogen concentration, corresponding to the ideal value $M_2$, is mixed with the helium in the gas mixer 11. This gas mixture is pumped directly to the analyzer 3, and the curve climbs steadily during measurement of this gas mixture until a constant measured value is reached in the analyzer 3. At the point in FIG. 2 referenced as $R_2$, the multipath valve 6 switches, so that the gas mixture from the measuring circuit is pumped to the analyzer 3 and measured there. The difference between the ideal value $S_2$ and the partial pressure $R_1$ of the gas to be measured after the gas exchange in the molten metal is negligible, so that the measurement can be terminated.

An additional shortening of the measurement time is possible by having the $S_2$ value determined though extrapolation, and thereby the switching of the multipath valve 6 can be done earlier. The $R_2$ value can also be determined through extrapolation, so that the overall time for determining the nitrogen content in the molten metal can be shortened.

In a similar manner it is possible to determine hydrogen in molten metals, e.g., in aluminum melt, whereby in this case the equations (4), (5) and (6) are used. For determination of hydrogen, argon or nitrogen is the preferred carrier gas. Also, it is not required for the determination of hydrogen to remove additional gas impurities with filters from the gas mixture from the molten metal.

The present invention may be embodied in other specific forms without departing from the spirit or essential attributes thereof and, accordingly, reference should be made to the appended claims, rather than to the foregoing specification as indicating the scope of the invention.

I claim:

1. A process for determining the concentration of a gas dissolved in a molten metal by measuring and calculating the partial pressure of the dissolved gas in a measuring cycle, comprising pumping a first portion of a carrier gas directly to at least one gas analyzer (3) for measurement of the carrier gas for calibration during a first measuring segment of the measuring cycle, substantially simultaneously pumping a second portion of the carrier gas to a measuring circuit for purging the measuring circuit and for uptake of dissolved gas from molten metal, said measuring circuit comprising a measuring probe (4) immersed in the molten metal (5) for conveying the carrier gas to the molten metal such that the carrier gas effects a gas exchange with the dissolved gas in the molten metal to form a sample gas mixture of carrier gas and dissolved gas,-pumping at least a portion of the sample gas mixture to the at least one gas analyzer (3) for measurement of the sample gas mixture immediately after calibration, and calculating the partial pressure of the dissolved gas from analyzer measurements of the carrier gas during calibration and the sample gas mixture as at least a first approximate value of the partial pressure of the dissolved gas.

2. The process according to claim 1, wherein a single gas analyzer is used for the measurements, said analyzer being alternatively connected to the first portion of carrier gas and to the portion of the sample gas mixture from the measuring circuit.

3. The process according to claim 1, wherein in a second measuring segment of the measuring cycle the first approximate value is set as an ideal value for a partial pressure of an initial gas mixture consisting of the carrier gas mixed with a gas the same as the dissolved gas, an actual value of a partial pressure of said initial gas mixture is measured in the analyzer, while simultaneously a portion of said initial gas mixture is pumped to the measuring circuit for purging and for uptake of the dissolved gas, after a gas exchange with the molten metal (5) a partial pressure of a resulting new sample gas mixture is measured, and thereafter a new approximate value is calculated for the partial pressure of the dissolved gas.

4. The process according to claim 3, wherein the second measuring segment is followed by at least one additional measuring segment, wherein the new approximate value is used as a new ideal value for a partial pressure to be set for an additional gas mixture consisting of the carrier gas mixed with a gas the same as the dissolved gas, wherein the additional gas mixture is selected according to a previous ideal value, the actual value of partial pressure of the additional gas mixture is measured in the analyzer (3), an actual value of partial pressure of a resulting additional sample gas mixture is measured after gas exchange with the molten metal, and thereafter an additional new approximate value is calculated for the partial pressure of the dissolved gas.

5. The process according to claim 3, wherein the dissolved gas is nitrogen and for measurement of nitrogen in the molten metal (5) in a sequential measuring cycle an ideal value for the partial pressure in the first measuring segment is calculated, wherein a constant (B) is derived from a preceding measuring cycle, which results from the equation:

$$R_1 - S_1 = \frac{(X - S_1)}{B} \quad (1)$$

wherein $R_1$ = partial pressure of the dissolved gas after the gas exchange in the molten metal in the first measuring segment;

$S_1$ = actual value of the partial pressure measured in the first segment for the gas mixed with the carrier gas which is pumped directly to the analyzer, the mixed gas being the same as the dissolved gas;

X = the measured value of the partial pressure of the dissolved gas in the molten metal, and wherein the setting of the ideal value ($M_2$) of the gas mixture to be set for the second measuring segment results from the equation:

$$S_1 + B(R_1 - S_1) = M_2. \quad (2)$$

6. The process according to claim 5, wherein an ideal value ($M_{j+1}$) for the partial pressure in the (j+1)th measuring segment results from the equation:

$$M_{j+1} = \frac{S_j(R_i - S_j) - S_i(R_j - S_j)}{R_1 - S_i - R_j + S_j} + S_j, \quad (3)$$

wherein i and j represent measurement numbers for the measuring segments, such that the (j)th measuring segment corresponds to the (i+n)th measuring segment, wherein i, j and n are whole numbers greater than zero.

7. The process according to claim 5, wherein the constant (B), calculated from a measuring segment in the sequential measuring cycle, is used in a respective sequential measuring cycle to derive a sulfur content of the molten metal (5).

8. The process according to claim 3, wherein the dissolved gas is hydrogen and for measurement of hydrogen in the molten metal (5) in a sequential measuring cycle an ideal value for the partial pressure in the first measuring segment is calculated, wherein a constant ($B^1$) is derived from a preceding measuring cycle, which results from the equation:

$$R_1 - S_1 = \frac{\sqrt{X} - \sqrt{S_1}}{B'} \quad (4)$$

wherein:

$R_1$ = partial pressure of the dissolved gas after the exchange in the molten metal in the first measuring segment;

$S_1$ = actual value of the partial pressure measured in the first segment for the gas mixed with the carrier gas which is pumped directly to the analyzer, the mixed gas being the same as the dissolved gas;

X = the measured value of the partial pressure of the dissolved gas in the molten metal, and wherein the setting of the ideal value ($M_2$) of the gas mixture to be set for the second measuring segment results from the equation:

$$[\sqrt{S_1} + B'(R_1 - S_1)]^2 = M_2. \quad (5)$$

9. The process according to claim 8, wherein an ideal value ($M_{j+1}$) for the partial pressure in the (j+1)th measuring segment is derived from the equation:

$$M_{j+1} = \frac{\sqrt{S_i}\,(R_i - S_i) - \sqrt{S_j}\,(R_i - S_i)}{R_j - S_j - R_i + S_i} + \sqrt{S_i}, \quad (6)$$

wherein i and j represent measurement numbers for the measuring segments, such that the (j)th measuring segment corresponds to the (i+n)th measuring segment, wherein i, j and n are whole numbers greater than 0.

10. The process according to claim 3, wherein based on a difference between the actual value of the partial pressure of the gas pumped directly to the analyzer (3) and the ideal value set for the gas mixture, a calibration of a mixing chamber (11) is obtained for determining the concentration for mixing the carrier gas with a gas the same as the dissolved gas for the next measuring segment.

11. The process according to claim 1, wherein the gas mixed with the carrier gas is a gas mixture of a gas the same as the carrier gas and the same gas as the dissolved gas.

12. The process according to claim 1, wherein the carrier gas and/or the mixture of the carrier gas and another gas, prior to the direct pumping into the analyzer (3), is cleaned of foreign substances by a filter (2).

13. The process according to claim 1, wherein the carrier gas or the gas mixture of the carrier gas with another gas is pulsatingly purged prior to the pumping into the analyzer (3) and/or the measuring circuit.

* * * * *